US006663581B1

(12) United States Patent  (10) Patent No.: US 6,663,581 B1
Calabrese                   (45) Date of Patent:     Dec. 16, 2003

(54) CERVICAL COLLAR HAVING MULTIPLE SIZES (76) Inventor: Salvatore Calabrese, 2109 S. Porter St., Philadelphia, PA (US) 19145

( * ) Notice: Subject to any disclaimer, the term of this patent is extended or adjusted under 35 U.S.C. 154(b) by 0 days.

(21) Appl. No.: 09/545,423

(22) Filed: Apr. 7, 2000

Related U.S. Application Data (60) Provisional application No. 60/128,519, filed on Apr. 9, 1999.

(51) Int. Cl.$^7$ .................................................. A61F 5/00
(52) U.S. Cl. ................................. 602/18; 128/DIG. 23
(58) Field of Search ............................... 602/5, 17, 18, 602/19; 128/846, DIG. 23

(56) References Cited

U.S. PATENT DOCUMENTS

| | | | | |
|---|---|---|---|---|
| 5,520,619 A | * | 5/1996 | Martin | 602/18 |
| 5,728,054 A | * | 3/1998 | Martin | 602/18 |
| 5,993,403 A | * | 11/1999 | Martin | 602/18 |
| 6,090,058 A | * | 7/2000 | Traut | 602/18 |

* cited by examiner

Primary Examiner—Michael A. Brown
(74) Attorney, Agent, or Firm—Schnader Harrison Segal & Lewis LLP; Kenneth R. DeRosa (57) ABSTRACT A cervical collar comprising a neckband fabricated from a substantially incompressible plastic material and including a front body section having a first substantially flat shape and being bendable into a second substantially tubular shape, the front body section having a central portion, a laterally extending first side portion, and an opposed laterally extending second side portion. The cervical collar also includes a mandible support fabricated from a substantially and compressible plastic material comprising a centrally located chin support, a laterally extending first side portion, and an opposed laterally extending second side portion and a clip associated with the cervical collar which is moveable from a first unengaged position to a second engaged position in collaboration with a plurality of protrusions located on the cervical collar which define a plurality of predefined positions between the mandible support and the neckband.

13 Claims, 10 Drawing Sheets

CERVICAL COLLAR HAVING MULTIPLE SIZES

This application claims the benefit of Provisional application No. 60/128,519 filed Apr. 9, 1999.

FIELD OF THE INVENTION

The present invention relates to orthopedic restraints and, in particular, to cervical collars.

THE BACKGROUND OF THE INVENTION

Light weight, plastic cervical collars come in a variety of designs. Traditional two-piece collars of the type shown in U.S. Pat. Nos. 3,756,226 and 4,886,052 use semi-circular body halves to provide cervical support. Despite their acknowledged successful performance, such two-piece collars are considered less desirable than other cervical collars for certain uses. In particular, such collars are considered undesirable for use in emergency vehicles where their relative bulk makes them difficult to store and because of the difficulties that arise from trying to slip a semi-circular rear collar half beneath the neck of an accident victim at the same time the emergency care providers are trying to immobilize the victim.

A number of cervical collars have been designed to respond to this need. These include, for example, those shown in U.S. Pat. Nos. 4,413,619; 4,712,540; 4,987,891; 5,060,637; and 5,215,517. Such collars typically include front and rear body sections cut from a non-foam, relatively stiff, yet flexible plastic sheet. A hybrid cervical collar is shown in U.S. Pat. No. 5,083,553 and has also been designed to respond to this need. The disclosed two-piece collar includes separate front and rear body sections cut from stiff, flexible plastic sheets.

The above-described collars are typically provided with an integrally attached chin support. This integrally attached chin support is mechanically fastened to the front body section, joining it at the distal ends at the chin support. However, the chin supports on such collars are typically provided as a flat structure, and must be folded into a cup-shape and mechanically fastened at the central portion of the folded front body section. This is due to the flat, resiliently flexible plastic sheet construction of the front body section and the chin support. Thus, these flat cervical collars with their mechanically attached chin support all suffer from a number of draw backs, especially with respect to the chin support area. In addition, these cervical collars are fabricated from stiff, flexible plastic sheets requiring that the chin support be mechanically fastened to the front body section. This mechanical fastening results in inadequate chin support, lack of stability, and decreased reliability. Due to the fabrication process used for existing collars, there is inadequate support under the chin. This inadequate support causes the head of the wearer to slip from the chin support into the interior of the collar.

At least one cervical collar has been designed to respond to this need. U.S. Pat. No. 5,622,529 discloses a substantially flat, one-piece and/or hybrid two-piece cervical collar having a unitary and/or molded central chin support. This unitary chin support design greatly simplifies the manufacturing process, simplifies the number of parts required, and reduces the mechanical fastening between the chin support and the front body section. The elimination of this mechanical connection decreases the flexibility of the collar and increases the rigidity of the chin support and results in a more stabilized cervical spine region of the wearer. It also results in a more reliable collar because the mechanical connection, which is prone to failure, could potentially break during continual use and may fail and render the collar useless. Also, the elimination of the mechanical connection between the chin and the collar decreases the manufacturing cost associated with providing such a connection and the manual labor required to accomplish the fastening process.

U.S. Pat. No. 5,622,529 also discloses, in FIG. 18, the use of a mandible support having a unitary chin cup is mechanically fastened to the front portion of the band of the collar. This embodiment of the '529 patent shows that the improved unitary chin support and mandible can be used in conjunction with virtually any existing collar band design.

More recently, cervical collar manufacturers have begun to adopt the chin cup and mandible support design shown in U.S. Pat. No. 5,622,529. For example, U.S. Pat. No. 5,795, 315 shows a cervical collar having a mandible support with a unitarily molded chin support. The mandible support is connected at its wing portioned to the front of the neck band. This simplified mandible support allows the cervical collar shown the '315 patent to be manufactured with a simplified design and lower construction cost and allows the collar to adopt the height-adjustment features of the prior art collars to produce a multiple-size collar. The multiple-size cervical collar of the '315 patent offers multiple sizes in a single collar and provides adequate support to the mandible as a result of the adoption of the unitarily formed chin support taught in U.S. Pat. No. 5,622,529.

Many prior cervical collars are known which include height-adjustment means for proper sizing of the collar. These include, for example, those shown in U.S. Pat. Nos. 5,728,054; 2,801,630; 2,911,970; 3,024,784; 3,285,244; 5,593,382; 3,916,885; and 3,060,930. Many of these collars employ height-adjustment means which are overly complex. Many of the designs include complex separately manufactured parts such as screws, bolts, pawls/ratchet teeth, snap connections, and hook and loop fasteners. Other height adjustment means, such as that shown in U.S. Pat. No. 5,795,315 also suffer from similar deficiencies. For example, the cantilevered protrusion of the '315 patent readily disengages from the complementary openings formed in the neck band when the collar is around the patient's neck, resulting in a collar which is incapable of supporting the neck of the wearer. In addition, the adjustment means of the '315 patent are spaced a significant distance from the center chin area of the collar and are located near the top edge of the collar, making adjustment of the collar on the patient's neck relatively difficult. In addition, the adjustment means of the '315 patent does not allow for ready adjustability the height of the collar since the made protrusion cannot be disengaged with the complementary hole under normal circumstances when the collar is around the patient's neck, and must be removed from the neck to adjust the size thereof. Lastly, the height adjustment means of the '315 patent requires a separate size indicating means which makes the sizing operation inconvenient.

Thus, there remains the need for a substantially flat, cervical collar having a height-adjustment means which is simple to use, does not require any complex manufacturing processes, does not readily disengage when the collar is bent around a patient's neck, and which includes an indicator for accurately sizing the collar.

SUMMARY OF THE INVENTION

The invention relates to a cervical collar having a neckband, a mandible support and a locking means. The neckband is fabricated from a substantially incompressible plastic material and comprises a front body section having a first substantially flat shape and being bendable into a second substantially tubular shape, the front body section has a central portion, a laterally extending first side portion, and an opposed laterally extending second side portion. The mandible support is fabricated from a substantially incompressible plastic material comprising a centrally located chin support, a laterally extending first side portion, and an opposed laterally extending second side portion. The locking means includes a clip associated with the cervical collar which is moveable from a first unengaged position to a second engaged position in collaboration with a plurality of protrusions located on the cervical collar which define a plurality of predefined positions between the mandible support and the neckband.

The plurality of protrusions may be formed on a face of the neckband and the clip is associated with the mandible support.

The neckband may have indicia disposed on the collar which indicate each of a plurality of collar sizes.

The protrusions may be formed in a pair of parallel columns on the front face of the neckband.

The clip may include at least one leg which engages between the protrusions to prevent relative motion or movement between the mandible support and the neckband.

The clip further may include a second leg which cooperates with a track formed on the collar to press the mandible support against the neckband to form a frictional fit there between.

A plurality of serrations may be formed on the adjacent faces of the mandible support and the neckband which engage each other and enhance the frictional fit between the mandible support and the neckband.

The clip may include at least one leg having an end which simulates a pointed arrow.

The clip may include an actuator head for facilitating the grasping of the clip by a user.

The clip may be fabricated so as to transfer the load of the user's chin on the mandible support to the neckband.

DETAILED DESCRIPTION OF THE PREFERRED EMBODIMENTS

Figure 1:
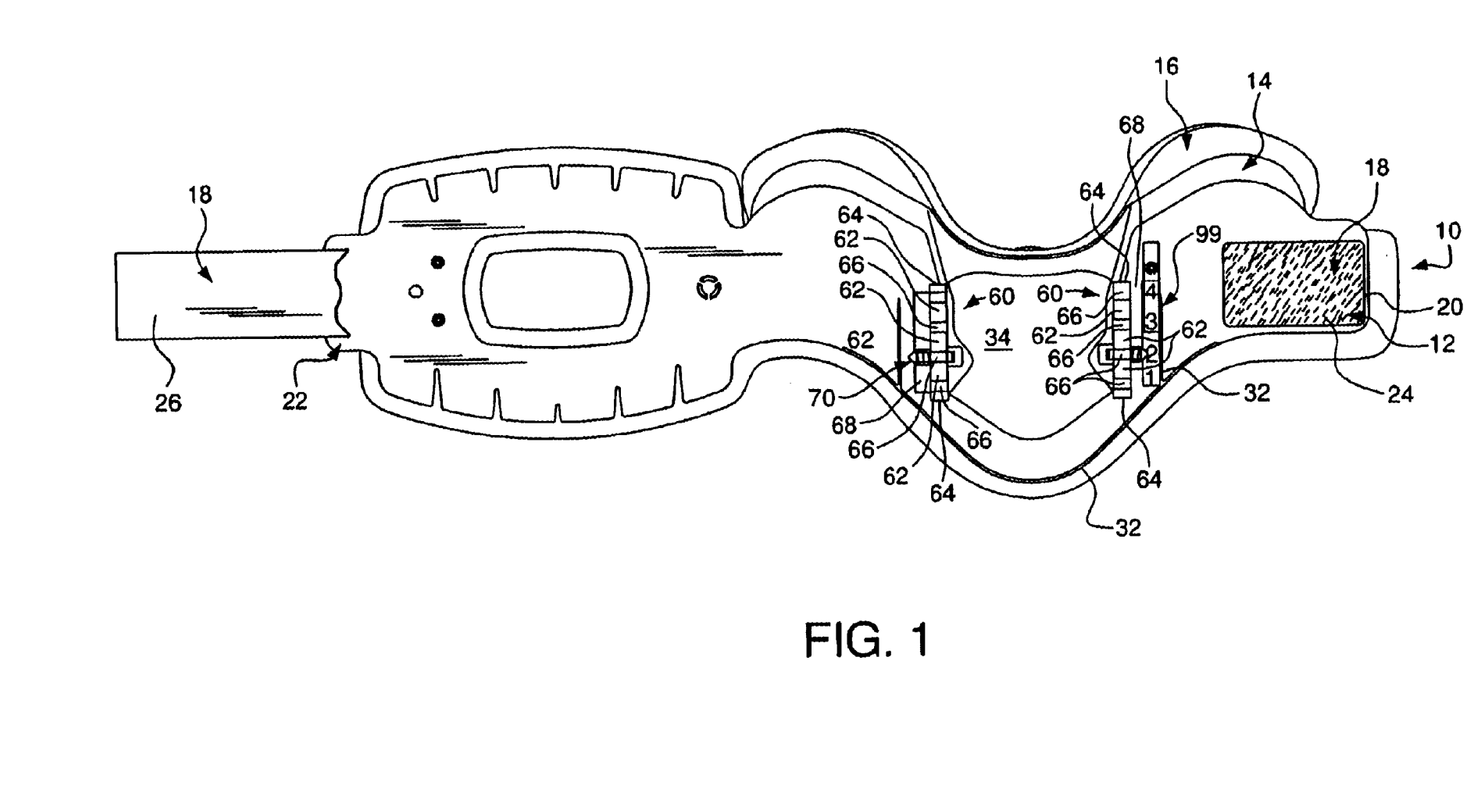
FIG. 1 is a front view of an embodiment of a cervical collar made in accordance with the present invention.

Referring now to the drawings, in which like reference numerals identify like elements throughout the several views, there is shown in FIG. 1, a multiple size cervical collar 10 of the present invention. The collar comprises a neck band 12, a mandible support 14, foam padding 16, and a fastener 18.

The neck band 12 and mandible support 14 are preferably fabricated by a molding process, and most preferably injection molded in one piece from a lightweight, flexibly resilient, substantially incompressible material, such as a suitable thermoplastic resin. Some suitable thermoplastic resins include high density polyethylene, polyurethane, polypropane, or the like.

Neck band 12 has a length and flexibility sufficient to be wrapped into a tubular shape, with the free edge 20 adjoining the opposite free edge 22 so as to form the neck band 12 into a generally tubular shape. The neck band 12 is preferably bendable, and even flexible, but sufficiently rigid to provide cervical support when wrapped into the tubular shape.

The fastener 18 preferably comprises a first fastener 24 attached to free end 20 and a second fastener 26, that cooperates with the first fastener 24, attached at the free edge 22. The fasteners 24 and 26 are coupled with and preferably fixedly attached by suitable mechanical or chemical means, such as adhesives, rivets, stitching, welding, integral molding, or the like, to the neck band 12. The fastener 24 is most preferably a loop-type fabric fastening strip. The fastener 24 is preferably attached to the neck band 12 by rivet fasteners. The fastener 26 is most preferably a hook-type fabric fastening strip which is adhesively attached to the neck band 12.

The flexible foam strips 16 are mounted to the inner face of the neck band 12 and the mandible support 14 and form the inner side of the collar 10 when it is wrapped into the tubular shape. The foam strips 16 are preferably shaped to cover the upper and lower portions of the front of the neck band 12 and the entire perimeter of the rear of the neck band 12. The foam strips 16 are preferably permanently fixed to the inner side of the neck band 12 and the mandible support 14 by adhesives and/or mechanical fasteners, most preferably thermoplastic rivet fasteners.

Figure 2:
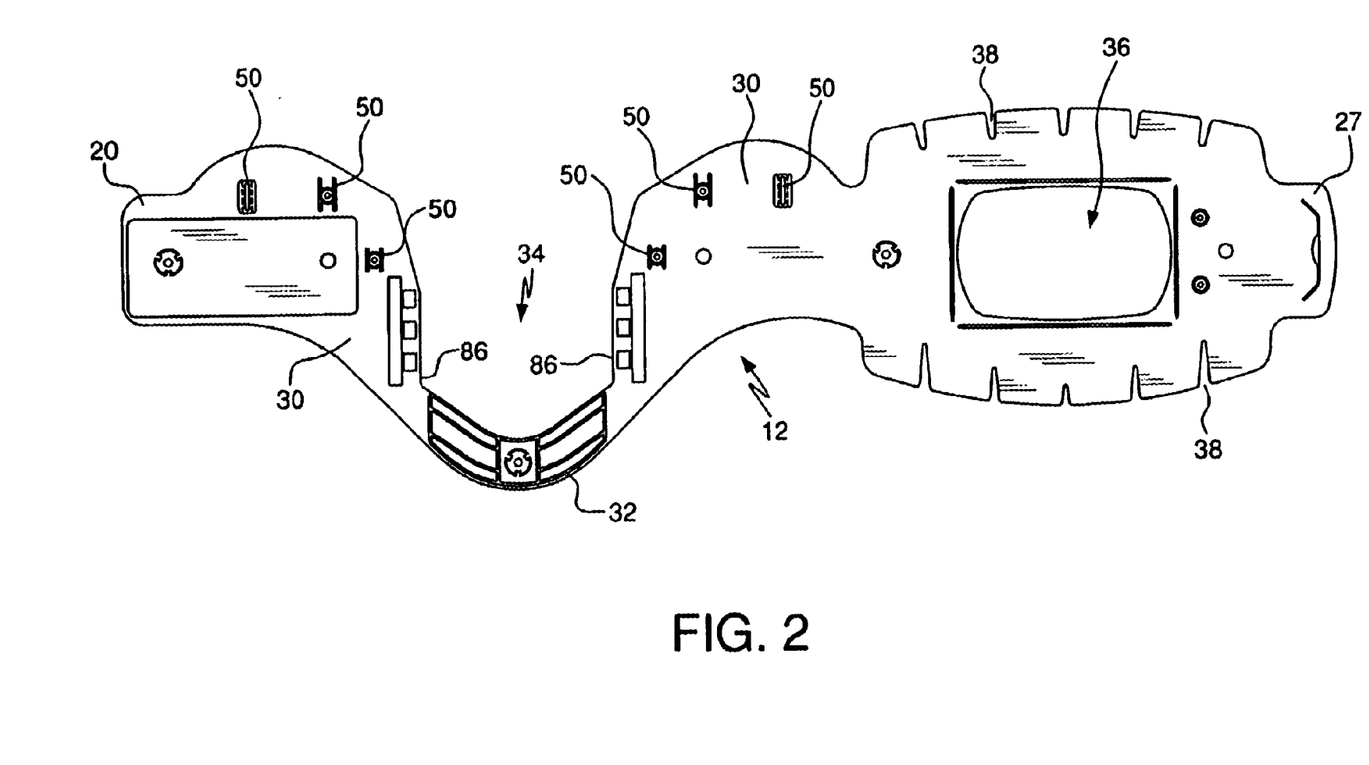
FIG. 2 is a back view of the neck band of the present invention.

As shown in FIGS. 1 and 2, the front portion of the neck band 12 includes a pair of laterally extending substantially flat side or wing portions 30. A large tracheal opening 34 is preferably medially located in the front section of the neck band between the side wing portions 30. Reinforcement ribs 32 or stiffening elements are formed on the neck band 12 to reinforce the body of the neck band and prevent it from tending to collapse. A spinal access opening 36 is formed in the back portion of the neck band 12. Relief slots or serrations 38 formed in the upper lower edges of the back portion of the neck band 12 allow the neck band to flex to the contour of the patient's neck.

Figure 3:
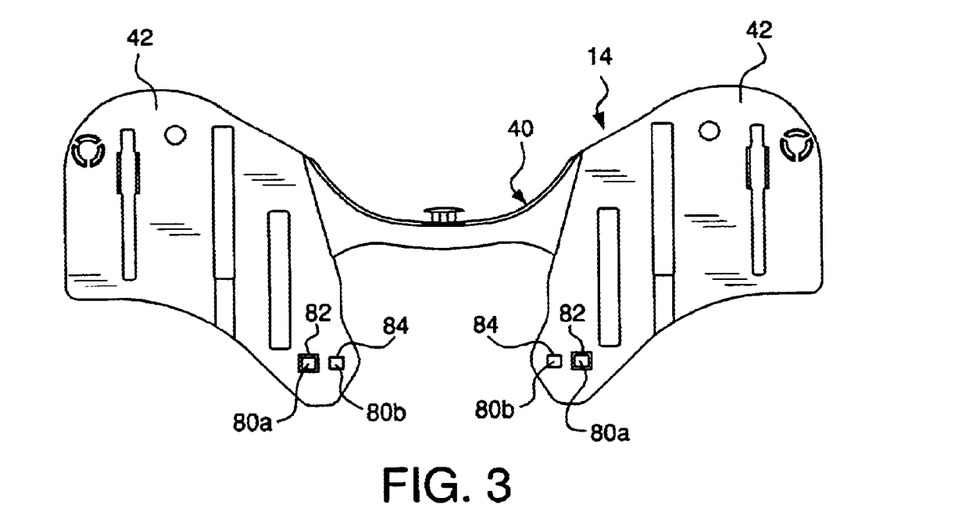
FIG. 3 is a front view of the mandible support of the present invention.
Figure 4:
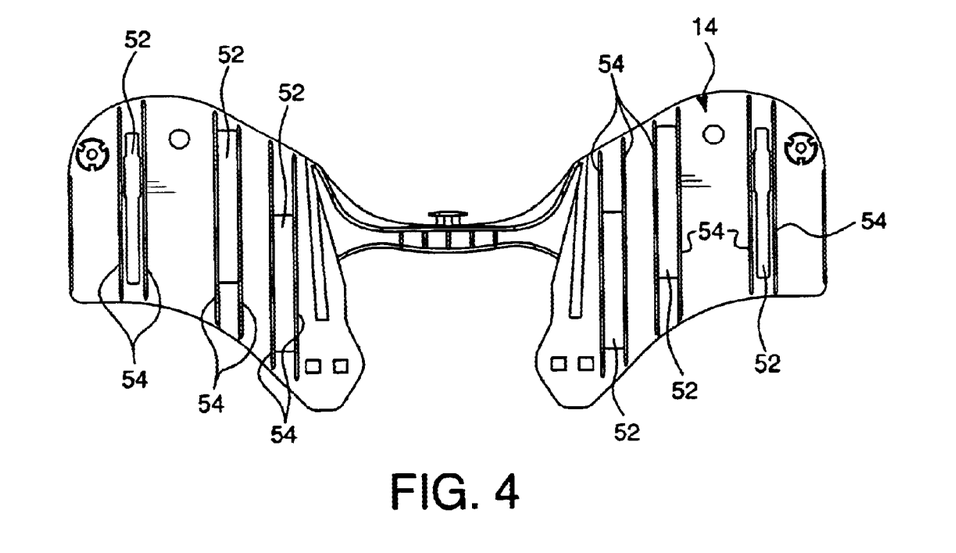
FIG. 4 is a back view of the mandible support of the present invention.

As best seen in FIGS. 1 and 3, the mandible support 14 includes a central chin support or cup 40 for supporting the wearer's chin. Extending laterally from either side the chin cup 40 is pair of laterally wings or side portions 42. The substantially planar side portions 42 of the mandible support 14 and the substantially planar side portions 30 of the neck band 12 are slidingly engaged with each other, permitting vertical height adjustment of the collar, as described in greater detail below.

The specifics of the cervical collar, in particular the specifics of the chin cup, are described in greater detail in U.S. Pat No. 5,622,529, which issued on Apr. 22, 1977, entitled "Flat Cervical Collar Having a Unitary Chin Support," which is incorporated herein by reference.

As best seen in FIG. 2, a plurality of male protruding sliders 50 extend from the back surface of the neck band 12. The male sliders 50 engage with corresponding parallel slots 52 formed in the wing portion 42 of the mandible support 14. The slider slots 52 may be stiffened with ribs 54 on their lateral edges. The slots 52 are sized and configured to cooperate with the male sliders 50 which protrude from the back portion of the neck band 12, so as to permit only vertical transitory movement between the mandible support 14 and the neck band 12. The relative position of the back side of the neck band and the mandible support, is fixed a locking means 60, which will be described in greater detail below.

Figure 5:
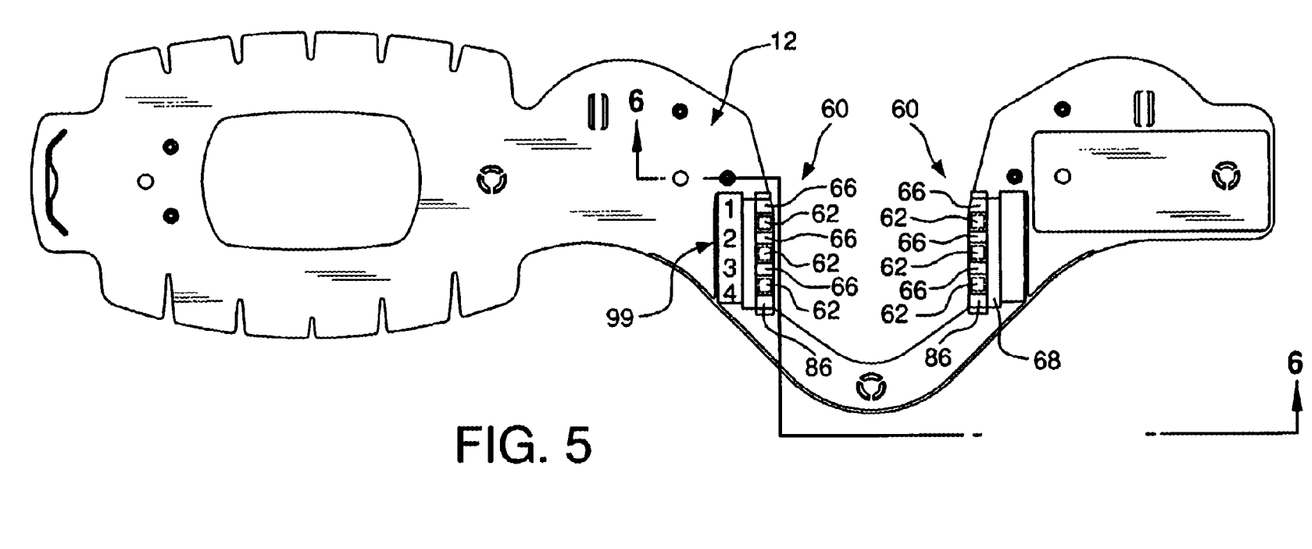
FIG. 5 is a front view of the neck band of the present invention.
Figure 6:
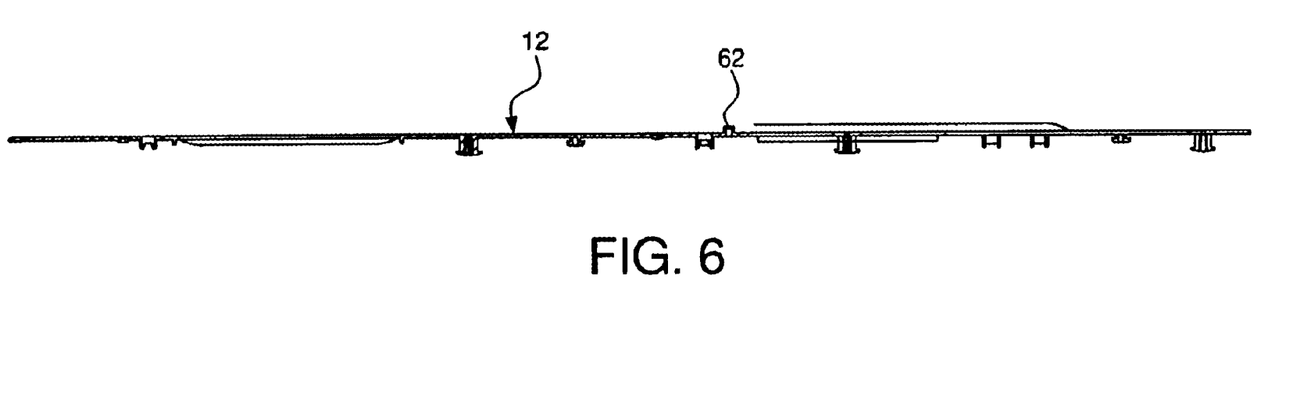
FIG. 6 is a cross-sectional view of the neck band of the present invention taken along line VI—VI of FIG. 5.

Referring now to FIGS. 1, 5 and 6 the locking means 60 is shown. The locking means 60 includes a series of vertically aligned rectangular blocks 62 which extend from the front face of the neck band 12. A column of these protruding blocks 62 are formed on either side of the tracheal opening 34. Each column of blocks 62 is bounded on it's upper and lower end by an additional half-height end protrusions 64. In this way, a slot 66 is formed between each of the blocking member 62 and between one of the end blocks 62 and the end protrusion 64.

The locking means 60 also includes an extended slot 68 which is adjacent to each column of protruding blocks 62.

Referring now to FIG. 3, the front surface of the mandible support 14 is shown. A pair of openings 80a and 80b are formed in the lower portion of the mandible support 14 on each side of the tracheal opening 34. Openings 80a may include a peripheral rib 82. Openings 80b are formed in an tab portion 84 which extends from the sidewall which forms the tracheal opening 34 of the mandible support. When the mandible support 14 is attached to the neck band 12, the opening 80a is aligned with the elongated slot 68, whereas the opening 80b on tab 82 extends past the edge 86 (best seen in FIG. 5) of the neck band 12 and is visible through the tracheal opening 34.

Figure 7:
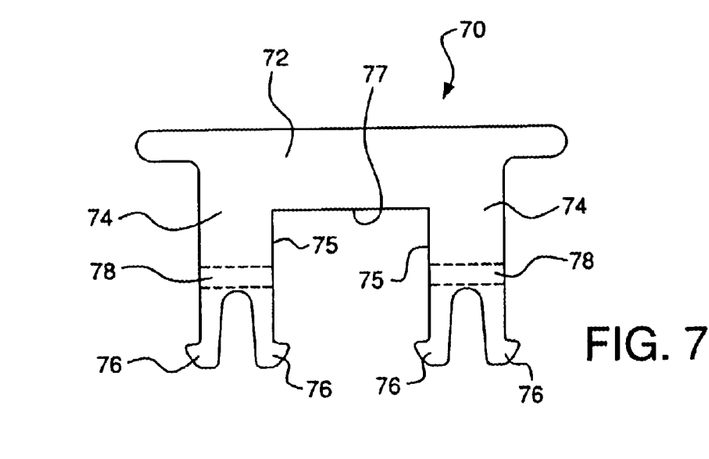
FIG. 7 is a front view of the U-shaped clip of the present invention.
Figure 8:
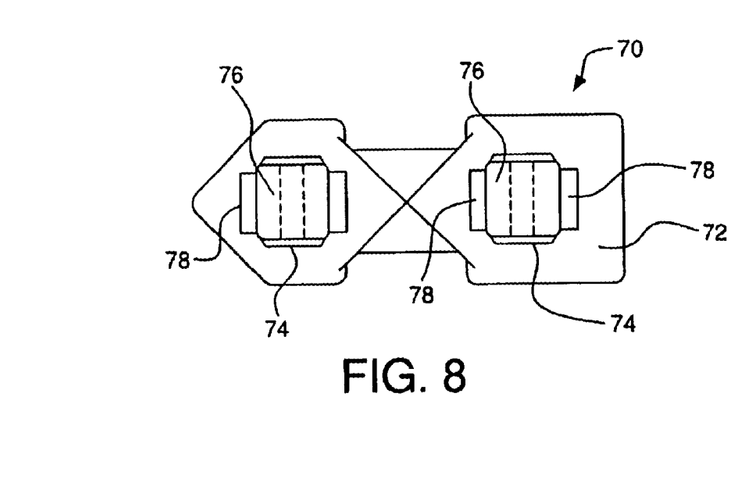
FIG. 8 is a back view of the clip of the present invention.
Figure 9:
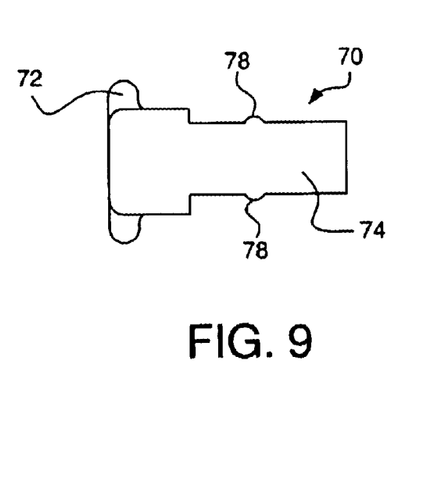
FIG. 9 is a side view of the clip of the present invention.

Referring now to FIG. 1, the locking means 60 also comprises a U shaped clip 70. The clip 70 is best seen in FIGS. 7–9 and includes an enlarged actuator head 72. A pair of legs 84 extend from the bottom surface of the head 72. The legs 74 are spaced such that the distance between the legs 74 is greater than the width of the blocks 62 which protrude from the front surface of the neck band 12. The distance between the inner surfaces 75 of the legs 74 allows the legs 74 to engage with the openings 80a and 80b formed in the mandible support 14. Wedge shaped locking members 76 are formed at the distal ends of the legs 74. The locking members 76 deflect inwardly when the legs 74 to engage the openings 80a and 80b. Once the locking members 76 clear the depth of the openings 80a and 80b, they will return to their normal configuration and are locked within the openings 80a and 80b and cannot be removed. A protrusion or detent 78 is formed intermediately around each leg 74. The detent 78 also engages with the openings 80a and 80b and allows the clip 70 to be removably engaged therewith.

The enlarged actuator head 72 may be manually manipulated by the wearer or applicator of the cervical collar to engage and disengage the legs 74 and detent 78 with the openings 80a and 82 of the mandible support 14. One side of the actuator head 72 has a triangular head such that the actuator simulates an arrow.

In use, the clip 70 is inserted into the front surface of the neck band 12 to engage the openings 80a and 80b. One of the legs 74 of the clip 70 extends through the elongated slot 68 of the neck band 12 to engage opening 80a, the other leg 74 of the clip 70 clears the inner edge 86 of the neck band 12 and engages with opening 80b. In this way, the clip 70 bridges the column 66 blocks 62. The distal locking members 76 retain the clip 70 within the openings 80a and 80b. The height of the actuator head 72 above the distal locking members 78 is sufficient that the bottom surface 77 of the actuator head will clear the protruding depth of the blocks 62.

When the mandible support 14 is vertically displaced by a user, the extending legs 74 of the clip 70 will ride within the elongated slot 68 and in the tracheal opening 70 near the edge 86. The rib 82 also rides within the slot 68. When a desired height is selected by a user, corresponding to the alignment of the actuator head 72 of the clip 70 with one of the slots 66 formed between the blocks 62, the clip 70 is depressed by the user so that the actuator head 72 engages one of the slots 66. When the clip 70 is depressed in this lower engaged position, the actuator head 72 will prevent vertical movement of the mandible support relative to the neck band 12. In this engaged position, the detents 78 will be engaged with the openings 80a and 80b to secure the actuator head in the engaged position. If subsequent adjustment is desired, the clip 70 can be removed by pulling the actuator head 72 away from the neck band 12, disengaging the protrusion detent 78 from the opening 80a and 80b. The clip 80 would still be retained within the openings 80a and 80b by virtue of the locking member 78, but the lowermost surface 77 of the actuator head 72 would now be in upper unengaged position and would clear the top of the blocks 62.

As best seen in FIGS. 1 and 5, indicia 99 may also be provided adjacent to each of the slots 68 to indicate a size of the cervical collar in each of the multiple positions obtainable by the collar. The triangular surface or arrow shaped head of the actuator 72 would point to one of the indicia markings.

Figure 10:
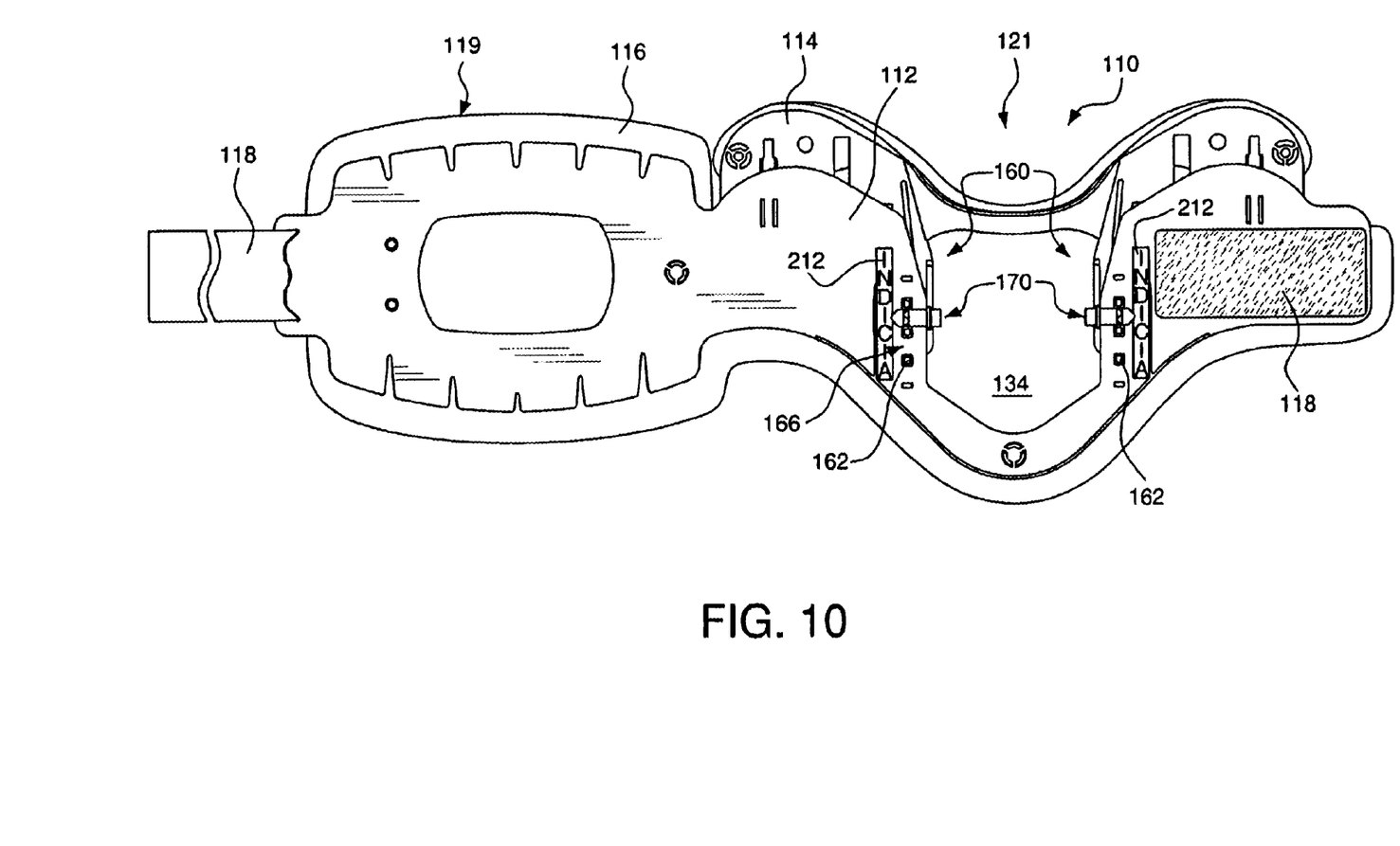
FIG. 10 is a front view of an alternate embodiment of a cervical collar made in accordance with the present invention.

An alternate version of the preferred invention is showed in the FIGS. 10–16. In FIG. 10, there is showing a multiple size cervical collar 110 which is similar to collar 10 with the exception of those features described below.

The collar 110 comprises a neckband 112, and mandible support 114, foam padding 116, and a fastener 118. The collar 114 has an asymmetrical shape in that the back portion 119 is not the same shape of the front portion 121 of the collar.

Figure 11:
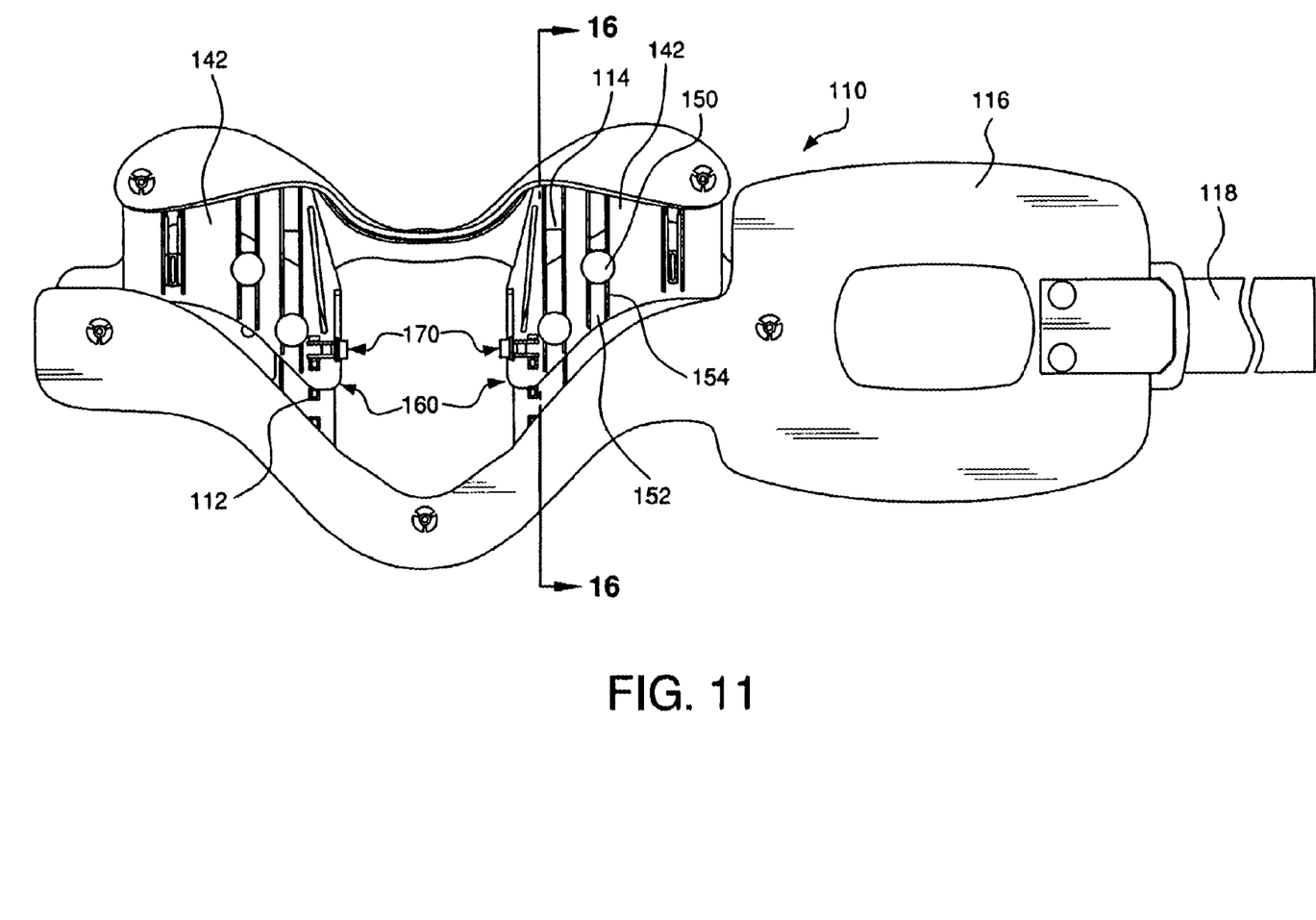
FIG. 11 is a back view of the cervical collar of FIG. 10.

As best seen in FIG. 11, a plurality of male sliders 150 extend from the back surface of the neckband 112. The male slides 150 engage with corresponding parallel slots 152 formed in the laterally extending portion 142 of the mandible support 114. The slider slots 152 may be stiffened with ribs 154 on their lateral edges. The slots 152 are sized and configured to cooperate with the male sliders 150 which protrude from the back portion of the neckband 112 so as to permit only vertical translational movement between the mandible support 114 and the neckband 112. The relative position of the backside of the neckband 112 and the mandible support 114, is fixed by a locking means 160 which will be described in greater detail below.

Figure 13:
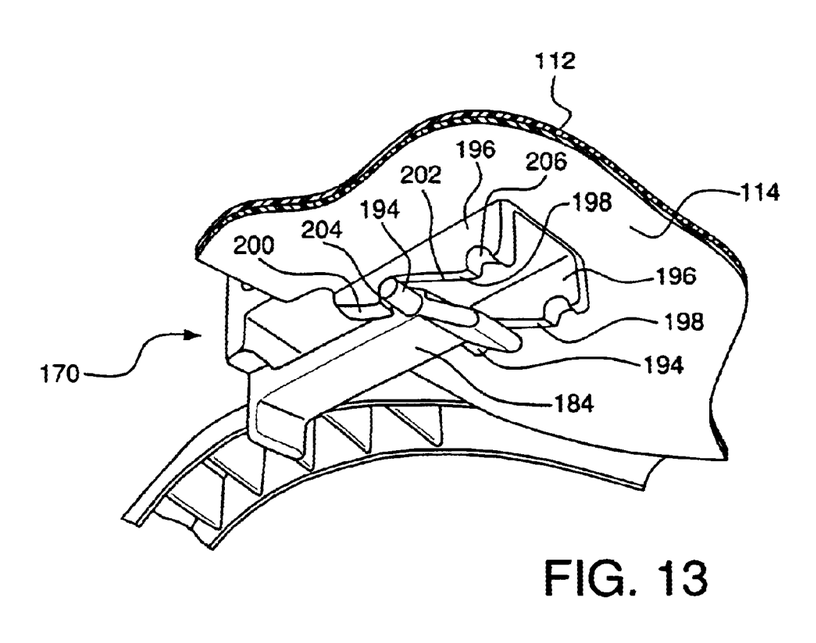
FIG. 13 is a partial enlarged isometric view of the back side of the cervical collar of FIG. 10 with the clip in the unengaged position.
Figure 14:
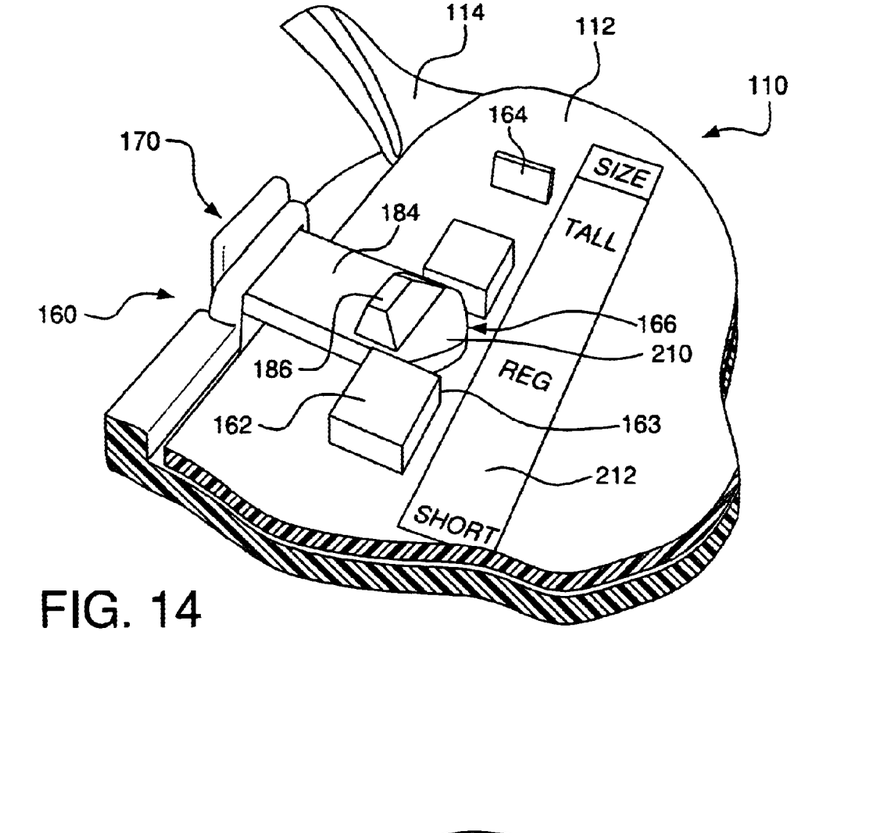
FIG. 14 is a partial enlarged isometric view of the front side of the cervical collar of FIG. 10 with clip in the engaged position.
Figure 15:
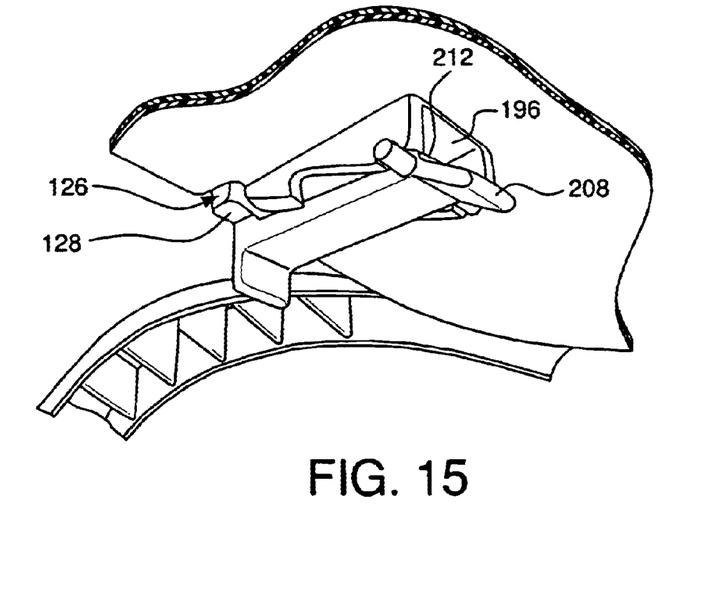
FIG. 15 is a partial enlarged isometric view of the back side of the cervical collar of FIG. 10 with the clip in the engaged position.

Referring now to FIGS. 13–15, the locking means 160 is shown. The locking means 160 includes a series of vertically aligned rectangular blocks 162 which extend from the front face of the neckband 112. A column of these protruding blocks 162 are formed on either side of the tracheal opening 134. Each column of blocks 162 is bounded on its upper and lower end by an additional protrusion 164. In this way, a slot 166 is formed between each of the blocks 162 and between one of the end blocks 162 and the end protrusion 164.

The mandible support 114 includes a laterally extending portion 179 which extends into the tracheal opening 134. Attached to the extending portion 179 is a protruding tab 180 which protrudes from the front face of the mandible support 114. An opening 182 is formed in the protruding tab 180.

The locking means 160 also comprises a generally U-shaped clip 170. The clip 170 includes an enlarged actuator head 172. A pair of legs 184 extend from the bottom surface of the head 172. The legs 184 are spaced apart sufficiently such that one of the legs 184 can extend through the opening 182 in the protruding tab 180, while the other leg 184 clears both the neckband 112 and the mandible support 114 such that the bottom leg 184 extends underneath the collar. The opening 182 of the protruding tab 180 is positioned such that when the clip 170 extends through the opening 182, the bottom side of the leg 184 will slide along the front face of the neckband 112. The width of the top leg 184 is sized to allow the leg 184 to engage any one of the slots 166.

The top leg 184 includes a protrusion 186 which cooperates with the protruding tab to prevent the clip 170 from disengaging with the protruding tab 180 once it is inserted therein. The protrusion 186 includes an angled front face 188 and a transverse back face 190. The inclined front face 188 of the protrusion 186 functions to cooperate with the opening 182 of the protruding tab 180 when the clip 170 is initially inserted therein to allow the clip 170 to slide into the opening 182. Once the clip 170 is inserted through the opening 182, the transverse back face 190 prevents the clip 170 from being withdrawn and unengaged from the opening 182. Similarly, the bottom face 192 of the actuator head 172 prevents the clip 170 from being inserted too far through the opening 182. Thus, it should be understood that the transverse back face 190 and the bottom face 192 act as stops which limit the positioning of the clip 170.

Referring now to FIG. 13, the end of the bottom leg 184 is provided with a pair of laterally extending protruding rods 194 which cooperate with a pair of tracks 196 formed on the back face of the mandible support 114. The tracks 196 are provided with a camming surface 198 which cooperates with the protruding rods 194 to form a cam/follower arrangement. The camming surface 198 includes the first inclined portion 200, a second inclined portion 202, a transverse portion 204, and a rounded groove portion 206.

When the clip 170 is initially inserted into the opening 182 of the protruding tab 180, the bottom leg 184 engages with the first inclined portion 200. As the clip 170 is pushed through the opening 182, the inclined front face 188 deflects the top wall of the protruding tab 180 as the clip 170 is inserted therein. While the front face 188 is slipping past the opening 182, the rod 194 are engaging the first inclined portion 200.

As soon as the protrusion 186 clears the opening 182, the protruding rods 194 finish riding up the first inclined portion 200 and fall onto the second inclined portion 202. At this point, the transverse portion 204 of the tracks 196 prevent the clip 170 from being disengaged with the collar. When the clip 170 is aligned with one of the slots 166, the clip 170 can be further inserted into the opening 182. As the clip 170 is pushed further into the opening 182, the protruding rods 194 ride up the second inclined portion 202 until the clip 170 is fully inserted into the opening 182 and the protruding rods 194 engage the rounded groove 206.

In FIGS. 13 and 14. In FIGS. 13 and 14, the clip 170 is fully inserted into the opening 182 and extends within one of the slots 166. As the protruding rods 194 engage the second inclined portion 202, the second inclined portion 202 serves to deflect the bottom leg 184 of the clip 170. The resiliency of the plastic leg 170 serves to press on the tracks 196 which in turn presses the mandible support 114 against the neckband 112 against the force of the opposite top leg 184. In this way, the legs 184 of the clip 170 cooperate with the camming track 196 to press the mandible support 114 against the neckband 112 when the clip 170 is fully engaged in the opening 182 and between one of the slots 166. This frictional fit serves to keep the mandible support 114 fixedly engaged with the neckband 112 when the clip 170 is fully engaged.

The bottom leg 184 is provided with an actuator and 208 which can be used by the wearer of the collar or the applier of the collar to disengage the clip 170 from the rounded grove 206, if the collar needs to be repositioned. In addition, the top leg 184 of the clip 170 is provided with a triangularly shaped end 210 which simulates an arrow or pointer. The pointer 210 is used with a strip of indicia 212 adjacent the protruding blocks 162 to inform the user of the proper size of the collar.

Figure 12:
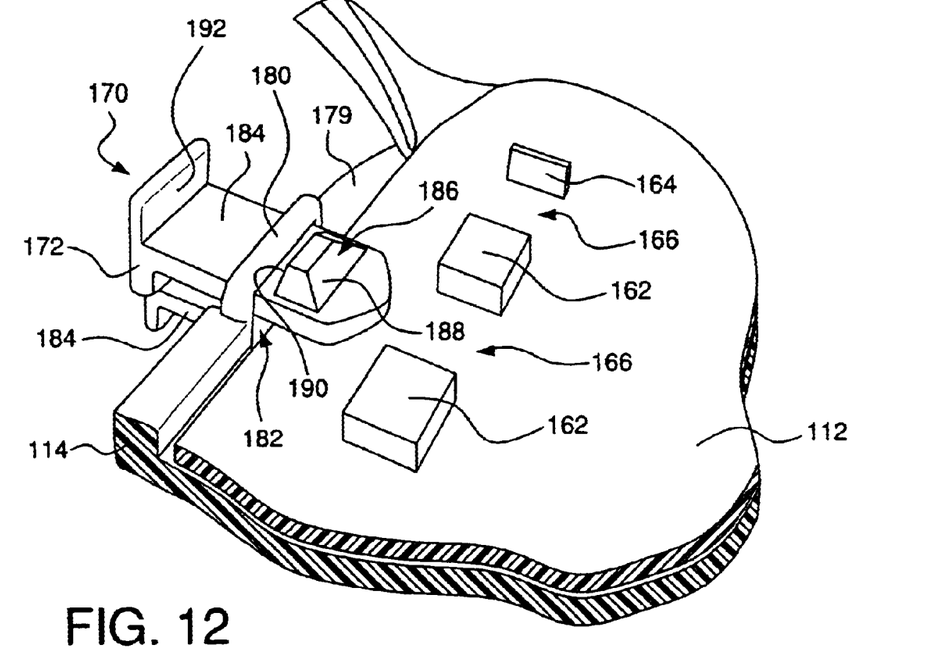
FIG. 12 is a partial enlarged isometric view of the front side of the cervical collar of FIG. 10 with clip in the unengaged position

Also, as best seen in FIG. K, the mandible support 114 is provided with a cut-out portion 126 which cooperates with an extending portion 128 of the clip 170 to further prevent displacing the mandible support relative to the neckband 112. In operation, the collar 110 functions as follows. The mandible support 114 is translated vertically with respect to the neckband 112 until the clip 170 is aligned with one of the slots 166. The user may utilize the indicia 212, as best seen in FIG. 14, to determine the proper sizing of the collar 110 as the mandible support 114 is manipulated. It should be understood that the mandible support 114 can only be manipulated or moved when the clip 170 is not engaged in the slots 166 as best seen in FIGS. 12 and 13.

When the user determines the proper sizing of the collar, he or she may then push the clips 170 to their engaged position by pushing on the actuator head 172 as best seen in FIGS. 14 and 15. As the user pushes the clips 170 into the slots 166, the camming rods 194 of the bottom leg 184 coact with the camming track 196 to press the mandible support 114 and the neckband 112 together.

The user may continue to push the clips into the openings 182 until the protruding rods 194 engage with the rounded groove 206 and the bottom face 192 of the actuator head engages with the protruding tab 180 to prevent further movement by the clip 170. The rounded groove 206 coacts with the protruding rod 194 to secure the clips 170 in the fully engaged position as shown in FIGS. 14 and 15.

In addition, the resiliency of the bottom leg 184, as it rides up the second incline surface 202 and falls into the rounded grove 206, produces an audible sound which indicates to the user that the clip is now fully engaged into the collar.

Once the clips 170 are fully engaged in the collar 110, the top leg 184 engages the top face 163 of the block 162 as it resides in one of the slots 166 to prevent further translational movement of the mandible support 114 as the force of the user's chin and the chin cup of the mandible support presses downwardly. It should also be understood that the clip 170 would also serve to prevent upward motion of the mandible support 114 since it is trapped between two blocks 162.

In addition, as best seen in FIG. 15, a small protrusion 212 which extends from the bottom leg 184 of the clip 170 engages with the inner walls of the tracks 196 to also permit translational movement of the mandible support 114. It should also be understood that the frictional fit between the mandible support 114 and the neckband 112 caused by the coaction of the legs of the clip 184 and the camming track 196 which presses the respective parts of the collar together also serves to prevent lateral motion there between.

Figure 16:
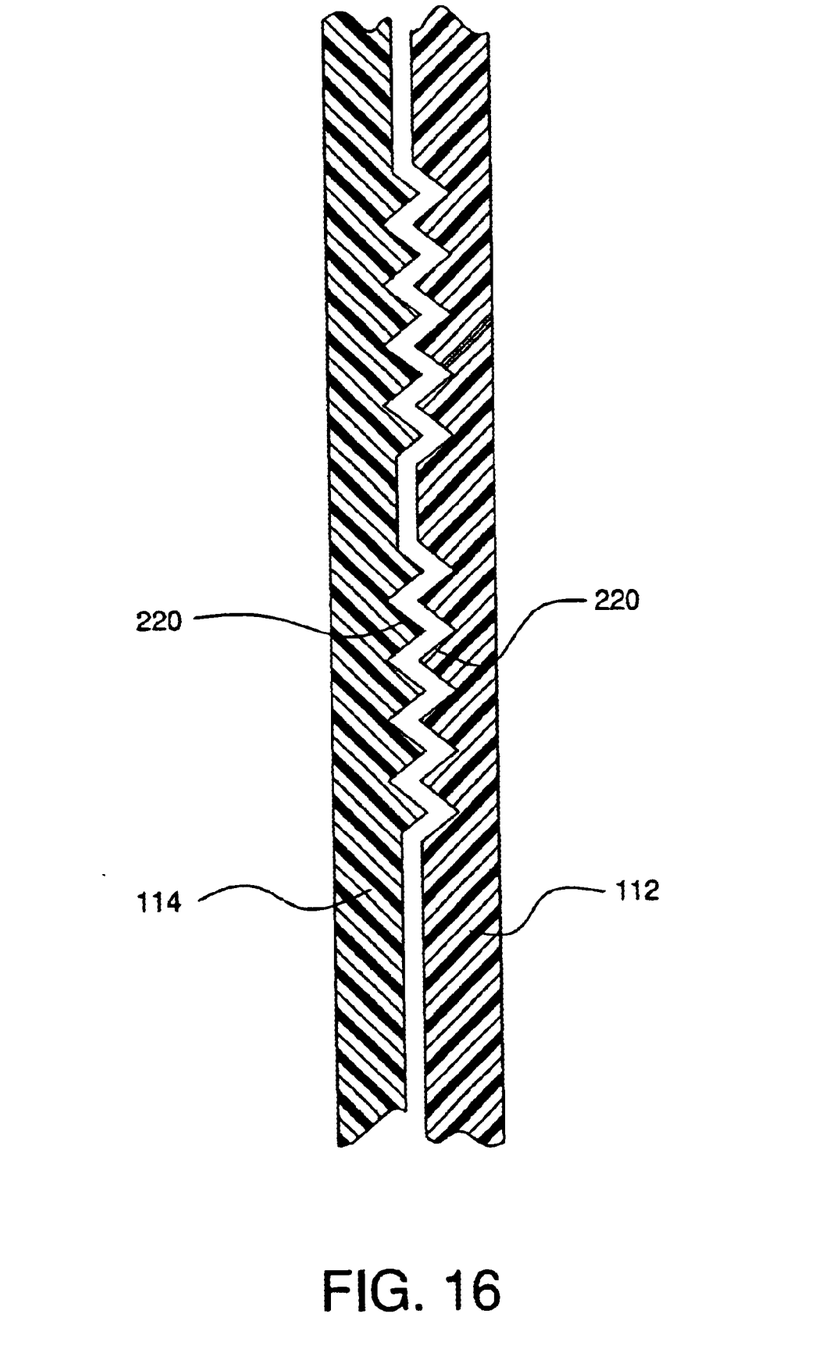
FIG. 16 is a partial cross sectional view taken along line 16—16 of FIG. 11.

As best seen in FIG. 16, a plurality of tracks of serrated teeth 220 may be provided on the back face of the neckband 112 and the front face of the mandible support 114 to further enhance the frictional fit of the cervical collar caused by the legs of the clip 184 and the camming track 196. These serrated teeth 220 would have a substantially triangular shape which would slide past each other when the clip 170 is not in the engaged position and would allow the mandible support 114 to slide past the neckband 112. When the clip 170 is in the engaged position, the serrated teeth 220 are pressed against each other to enhance the frictional fit between the mandible support 114 and neckband 112.

While certain prefer embodiments and various modifications thereto have been described or suggested, other changes in these preferred embodiments will occur to those ordinarily skilled in the art which do not depart from the broad inventive concepts of the present invention.

What is claimed is:

1. A cervical collar comprising:
   a neckband fabricated from a substantially incompressible plastic material and comprising a front body section having a first substantially flat shape and being bendable into a second substantially tubular shape, the front body section having a central portion, a laterally extending first side portion, and an opposed laterally extending second side portion;
   a mandible support fabricated from a substantially incompressible plastic material comprising a centrally located chin support, a laterally extending first side portion, and an opposed laterally extending second side portion; and
   a clip associated with the cervical collar which is moveable from a first unengaged position to a second engaged position in collaboration with a plurality of protrusions located on the cervical collar which define a plurality of predefined positions between the mandible support and the neckband, wherein the protrusions protrude outwardly from the face of the cervical collar and wherein the thickness of the protrusions is greater than the thickness of the neckband.

2. The cervical collar as set forth in claim 1, wherein the plurality of protrusions are formed on a face of the neckband and the clip is associated with the mandible support.

3. The cervical collar as set forth in claim 1, wherein the neckband has indicia disposed on the collar which indicate each of a plurality of collar sizes.

4. The cervical collar as set forth in claim 1, wherein the protrusions are formed in a pair of parallel columns on the front face of the neckband.

5. The cervical collar as set forth in claim 1, wherein the clip comprises at least one leg which engages between the protrusions to prevent relative motion or movement between the mandible support and the neckband.

6. The cervical collar as set forth in claim 5, wherein the clip further comprises a second leg which cooperates with a track formed on the collar to press the mandible support against the neckband to form a frictional fit there between.

7. The cervical collar as set forth in claim 1, further comprising a plurality of serrations formed on the adjacent faces of the mandible support and the neckband which engage each other and enhance the frictional fit between the mandible support and the neckband.

8. The cervical collar as set forth in claim 1, wherein the clip comprises at least one leg having an end which simulates a pointed arrow.

9. The cervical collar as set forth in claim 1, wherein the clip further comprises an actuator head for facilitating the grasping of the clip by a user.

10. The cervical collar as set forth in claim 1, wherein the clip transfers the load of the user's chin on the mandible support to the neckband.

11. A cervical collar comprising:
    a neckband fabricated from a substantially incompressible plastic material and comprising a front body section having a first substantially flat shape and being bendable into a second substantially tubular shape, the front body section having a central portion, a laterally extending first side portion, and an opposed laterally extending second side portion;
    a mandible support fabricated from a substantially incompressible plastic material comprising a centrally located chin support, a laterally extending first side portion, and an opposed laterally extending second side portion; and
    a clip associated with the cervical collar which is moveable from a first unengaged position to a second engaged position in collaboration with a plurality of protrusions located on the cervical collar which define a plurality of predefined positions between the mandible support and the neckband, wherein the clip comprises at least one leg which engages between the protrusions to prevent relative motion or movement between the mandible support and the neckband, and wherein the clip further comprises a second leg which cooperates with a track formed on the collar to press the mandible support against the neckband to form a frictional fit there between.

12. A cervical collar comprising:
    a neckband fabricated from a substantially incompressible plastic material and comprising a front body section having a first substantially flat shape and being bendable into a second substantially tubular shape, the front body section having a central portion, a laterally extending first side portion, and an opposed laterally extending second side portion;
    a mandible support fabricated from a substantially incompressible plastic material comprising a centrally located chin support, a laterally extending first side portion, and an opposed laterally extending second side portion;
    a clip associated with the cervical collar which is moveable from a first unengaged position to a second engaged position in collaboration with a plurality of protrusions located on the cervical collar which define a plurality of predefined positions between the mandible support and the neckband; and a plurality of serrations formed on the adjacent faces of the mandible support and the neckband which engage each other and enhance the frictional fit between the mandible support and the neckband.

13. A cervical collar comprising:

a neckband fabricated from a substantially incompressible plastic material and comprising a front body section having a first substantially flat shape and being bendable into a second substantially tubular shape, the front body section having a central portion, a laterally extending first side portion, and an opposed laterally extending second side portion;

a mandible support fabricated from a substantially incompressible plastic material comprising a centrally located chin support, a laterally extending first side portion, and an opposed laterally extending second side portion;

a clip associated with the cervical collar which is moveable from a first unengaged position to a second engaged position in collaboration with a plurality of protrusions located on the cervical collar which define a plurality of predefined positions between the mandible support and the neckband, wherein the clip comprises at least one leg having an end which simulates a pointed arrow.

* * * * *